US 8,246,648 B2

(12) United States Patent
Tekulve

(10) Patent No.: US 8,246,648 B2
(45) Date of Patent: Aug. 21, 2012

(54) REMOVABLE VENA CAVA FILTER WITH IMPROVED LEG

(75) Inventor: Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 143 days.

(21) Appl. No.: 12/267,769

(22) Filed: Nov. 10, 2008

(65) Prior Publication Data

US 2010/0121373 A1    May 13, 2010

(51) Int. Cl.
*A61M 29/00* (2006.01)
(52) U.S. Cl. ................................... 606/200
(58) Field of Classification Search ............ 606/200, 606/198, 108; 623/1.36, 1.13; 604/104–107
See application file for complete search history.

(56) References Cited

U.S. PATENT DOCUMENTS

| | | | |
|---|---|---|---|
| 2,281,448 A | 4/1942 | Mathey |
| 3,137,298 A | 6/1964 | Glassman |
| 3,174,851 A | 3/1965 | Buehler |
| 3,334,629 A | 8/1967 | Cohn |
| 3,540,431 A | 11/1970 | Mobin-Uddin |
| 3,868,956 A | 3/1975 | Alfidi et al. |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,655,771 A | 4/1987 | Wallsten |
| 4,665,906 A | 5/1987 | Jervis |
| 4,688,553 A | 8/1987 | Metals |
| 4,727,873 A | 3/1988 | Mobin-Uddin |
| 4,759,757 A | 7/1988 | Pinchuk |
| 4,781,177 A | 11/1988 | Lebigot |
| 4,793,348 A | 12/1988 | Palmaz |
| 4,817,600 A | 4/1989 | Herms et al. |
| 4,830,003 A | 5/1989 | Wolff et al. |

(Continued)

FOREIGN PATENT DOCUMENTS

DE    003417738    11/1985

(Continued)

OTHER PUBLICATIONS

Morris Simon, M.D. et al., A Vena Cava Filter Using Thermal Shape Memory Alloy, Oct. 1977, 89-94.

(Continued)

*Primary Examiner* — Elizabeth Houston
(74) *Attorney, Agent, or Firm* — Brinks Hofer Gilson & Lione

(57) ABSTRACT

A removable filter for capturing thrombi in a blood vessel. The filter has primary struts with first ends attached together along a longitudinal axis. Each primary strut has a body member extending from its first end along the longitudinal axis to an anchoring hook. Each primary strut is configured to move relative to the longitudinal axis between an expanded state and a collapsed state. At least one primary strut has a resistant portion next to the anchoring hook. The resistant portion is configured to contact the blood vessel in the expanded state. The filter also has secondary struts. The secondary struts have proximal ends attached together along the longitudinal axis and distal ends located radially from the longitudinal axis in the expanded state. The secondary struts are configured to engage the blood vessel to centralize the filter in the expanded state in the blood vessel.

16 Claims, 6 Drawing Sheets

U.S. PATENT DOCUMENTS

| | | | |
|---|---|---|---|
| 4,832,055 A | 5/1989 | Palestrant |
| 4,856,516 A | 8/1989 | Hillstead |
| 4,873,978 A | 10/1989 | Ginsburg |
| 4,943,297 A | 7/1990 | Saveliev et al. |
| 4,950,227 A | 8/1990 | Savin et al. |
| 4,954,126 A | 9/1990 | Wallsten |
| 4,957,501 A | 9/1990 | Lahille et al. |
| 4,969,891 A | 11/1990 | Gewertz |
| 4,990,156 A | 2/1991 | Lefebvre |
| 5,037,377 A | 8/1991 | Alonso |
| 5,059,205 A | 10/1991 | El-Nounou et al. |
| 5,061,275 A | 10/1991 | Wallsten et al. |
| 5,067,957 A | 11/1991 | Jervis |
| 5,071,407 A | 12/1991 | Termin et al. |
| 5,108,418 A | 4/1992 | Lefebvre |
| 5,108,419 A | 4/1992 | Reger et al. |
| 5,133,733 A | 7/1992 | Rasmussen et al. |
| 5,135,516 A | 8/1992 | Sahatjian et al. |
| 5,147,379 A | 9/1992 | Sabbaghian et al. |
| 5,152,777 A | 10/1992 | Goldberg et al. |
| 5,160,342 A | 11/1992 | Reger et al. |
| 5,190,546 A | 3/1993 | Jervis |
| 5,217,484 A | 6/1993 | Marks |
| 5,221,261 A | 6/1993 | Termin et al. |
| 5,224,953 A | 7/1993 | Morgentaler |
| 5,234,458 A | 8/1993 | Metais |
| 5,242,462 A | 9/1993 | El-Nounou et al. |
| 5,300,086 A | 4/1994 | Gory et al. |
| 5,304,121 A | 4/1994 | Sahatjian |
| 5,304,200 A | 4/1994 | Spaulding |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,413,586 A | 5/1995 | Dibie et al. |
| 5,421,832 A | 6/1995 | Lefebvre |
| 5,476,508 A | 12/1995 | Amstrup |
| 5,527,338 A | 6/1996 | Purdy |
| 5,540,712 A | 7/1996 | Kleshinski et al. |
| 5,549,626 A | 8/1996 | Miller et al. |
| 5,549,629 A | 8/1996 | Thomas et al. |
| 5,601,595 A | 2/1997 | Smith |
| 5,626,605 A | 5/1997 | Irie et al. |
| 5,630,801 A | 5/1997 | Roussigne et al. |
| 5,634,942 A | 6/1997 | Chevillon et al. |
| 5,649,906 A | 7/1997 | Gory et al. |
| 5,649,953 A | 7/1997 | Lefebvre |
| 5,669,933 A | 9/1997 | Simon et al. |
| 5,681,347 A | 10/1997 | Cathcart et al. |
| 5,683,411 A | 11/1997 | Kavteladze et al. |
| 5,695,519 A | 12/1997 | Summers et al. |
| 5,709,704 A | 1/1998 | Nott et al. |
| 5,720,764 A | 2/1998 | Naderlinger |
| 5,725,550 A | 3/1998 | Nadal |
| 5,746,767 A | 5/1998 | Smith |
| 5,755,778 A | 5/1998 | Kleshinski |
| 5,755,790 A | 5/1998 | Chevillon et al. |
| 5,776,162 A | 7/1998 | Kleshinski |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,836,968 A | 11/1998 | Simon et al. |
| 5,836,969 A | 11/1998 | Kim et al. |
| 5,843,244 A | 12/1998 | Pelton et al. |
| 5,853,420 A | 12/1998 | Chevillon et al. |
| 5,895,399 A | 4/1999 | Barbut et al. |
| 5,902,317 A | 5/1999 | Kleshinski et al. |
| 5,916,235 A | 6/1999 | Guglielmi |
| 5,928,260 A | 7/1999 | Chin et al. |
| 5,928,261 A | 7/1999 | Ruiz |
| 5,932,035 A | 8/1999 | Koger et al. |
| 5,938,683 A | 8/1999 | Lefebvre |
| 5,951,585 A | 9/1999 | Cathcart et al. |
| 5,961,546 A | 10/1999 | Robinson et al. |
| 5,976,172 A | 11/1999 | Homsma et al. |
| 5,984,947 A | 11/1999 | Smith |
| 6,007,557 A | 12/1999 | Ambrisco et al. |
| 6,007,558 A | 12/1999 | Ravenscroft et al. |
| 6,013,093 A | 1/2000 | Nott et al. |
| 6,077,274 A | 6/2000 | Ouchi et al. |
| 6,080,178 A | 6/2000 | Meglin |
| 6,086,610 A | 7/2000 | Duerig et al. |
| 6,126,673 A | 10/2000 | Kim et al. |
| 6,129,755 A | 10/2000 | Mathis et al. |
| 6,146,404 A | 11/2000 | Kim et al. |
| 6,152,144 A | 11/2000 | Lesh et al. |
| 6,156,055 A | 12/2000 | Ravenscroft |
| 6,156,061 A | 12/2000 | Wallace et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,193,739 B1 | 2/2001 | Chevillon et al. |
| 6,221,102 B1 | 4/2001 | Baker et al. |
| 6,231,589 B1 | 5/2001 | Wessman et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,088 B1 | 6/2001 | Lowery |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,900 B1 | 8/2001 | Nott et al. |
| 6,273,901 B1 | 8/2001 | Whitcher et al. |
| 6,277,139 B1 | 8/2001 | Levinson et al. |
| 6,287,315 B1 | 9/2001 | Wijeratne et al. |
| 6,287,329 B1 | 9/2001 | Duerig et al. |
| 6,306,163 B1 | 10/2001 | Fitz |
| 6,312,454 B1 | 11/2001 | Stockel et al. |
| 6,312,455 B2 | 11/2001 | Duerig et al. |
| 6,325,815 B1 | 12/2001 | Kusleika et al. |
| 6,331,183 B1 | 12/2001 | Suon |
| 6,342,062 B1 | 1/2002 | Suon et al. |
| 6,342,063 B1 | 1/2002 | DeVries et al. |
| 6,342,067 B1 | 1/2002 | Mathis et al. |
| 6,346,116 B1 | 2/2002 | Brooks et al. |
| 6,364,895 B1 | 4/2002 | Greenhalgh |
| 6,391,044 B1 | 5/2002 | Yadav et al. |
| 6,391,045 B1 | 5/2002 | Kim et al. |
| 6,436,120 B1 | 8/2002 | Meglin |
| 6,436,121 B1 | 8/2002 | Blom |
| 6,447,530 B1 | 9/2002 | Ostrovsky et al. |
| 6,461,370 B1 | 10/2002 | Gray et al. |
| 6,468,290 B1 | 10/2002 | Weldon et al. |
| 6,482,222 B1 | 11/2002 | Bruckheimer et al. |
| 6,485,502 B2 | 11/2002 | DonMichael et al. |
| 6,506,205 B2 | 1/2003 | Goldberg et al. |
| 6,511,503 B1 | 1/2003 | Burkett et al. |
| 6,517,559 B1 | 2/2003 | O'Connell |
| 6,527,962 B1 | 3/2003 | Nadal |
| 6,540,767 B1 * | 4/2003 | Walak et al. ............... 606/200 |
| 6,551,342 B1 | 4/2003 | Shen et al. |
| 6,558,404 B2 | 5/2003 | Tsukernik |
| 6,569,183 B1 | 5/2003 | Kim et al. |
| 6,579,303 B2 | 6/2003 | Amplatz |
| 6,582,447 B1 | 6/2003 | Patel et al. |
| 6,589,266 B2 | 7/2003 | Whitcher et al. |
| 6,602,226 B1 | 8/2003 | Smith et al. |
| 6,616,680 B1 | 9/2003 | Thielen |
| 6,638,294 B1 | 10/2003 | Palmer |
| 6,652,558 B2 | 11/2003 | Patel et al. |
| 6,685,722 B1 | 2/2004 | Rosenbluth et al. |
| 6,726,621 B2 | 4/2004 | Suon et al. |
| 6,972,025 B2 | 12/2005 | WasDyke |
| 7,279,000 B2 | 10/2007 | Cartier et al. |
| 7,323,003 B2 | 1/2008 | Lowe |
| 7,338,512 B2 | 3/2008 | McGuckin, Jr. et al. |
| 2001/0000799 A1 | 5/2001 | Wessman et al. |
| 2001/0011181 A1 | 8/2001 | DiMatteo |
| 2001/0023358 A1 | 9/2001 | Tsukernik |
| 2001/0034547 A1 | 10/2001 | Hall et al. |
| 2001/0034548 A1 | 10/2001 | Vrba et al. |

| | | | | | | |
|---|---|---|---|---|---|---|
| 2001/0037126 A1 | 11/2001 | Stack et al. | | 2006/0095068 A1 | 5/2006 | WasDyke et al. |
| 2001/0039432 A1 | 11/2001 | Whitcher et al. | | 2006/0100660 A1 | 5/2006 | Osborne et al. |
| 2002/0002401 A1 | 1/2002 | McGuckin, Jr. et al. | | 2007/0005095 A1 | 1/2007 | Osborne et al. |
| 2002/0016624 A1 | 2/2002 | Patterson et al. | | | | |
| 2002/0032460 A1 | 3/2002 | Kusleika et al. | | | | |
| 2002/0039445 A1 | 4/2002 | Abe et al. | | | | |
| 2002/0055767 A1 | 5/2002 | Forde et al. | | | | |
| 2002/0087187 A1 | 7/2002 | Mazzocchi et al. | | | | |
| 2002/0099431 A1 | 7/2002 | Armstrong et al. | | | | |
| 2002/0116024 A1 | 8/2002 | Goldberg et al. | | | | |
| 2002/0133217 A1 | 9/2002 | Sirhan et al. | | | | |
| 2002/0138097 A1 | 9/2002 | Ostrovsky et al. | | | | |
| 2002/0156520 A1 | 10/2002 | Boylan et al. | | | | |
| 2002/0161393 A1 | 10/2002 | Demond et al. | | | | |
| 2002/0169474 A1 | 11/2002 | Kusleika et al. | | | | |
| 2002/0169495 A1 | 11/2002 | Gifford et al. | | | | |
| 2002/0183782 A1 | 12/2002 | Tsugita et al. | | | | |
| 2002/0193827 A1 | 12/2002 | McGuckin, Jr. et al. | | | | |
| 2002/0193828 A1 | 12/2002 | Griffin et al. | | | | |
| 2002/0193874 A1 | 12/2002 | Crowley | | | | |
| 2003/0018343 A1 | 1/2003 | Mathis | | | | |
| 2003/0028238 A1 | 2/2003 | Burkett et al. | | | | |
| 2003/0040772 A1 | 2/2003 | Hyodoh et al. | | | | |
| 2003/0055481 A1 | 3/2003 | McMorrow | | | | |
| 2003/0069596 A1 | 4/2003 | Eskuri | | | | |
| 2003/0074019 A1 | 4/2003 | Gray et al. | | | | |
| 2003/0078614 A1 | 4/2003 | Salahieh et al. | | | | |
| 2003/0083692 A1 | 5/2003 | Vrba et al. | | | | |
| 2003/0097145 A1 | 5/2003 | Goldberg et al. | | | | |
| 2003/0105484 A1 | 6/2003 | Boyle et al. | | | | |
| 2003/0109897 A1 | 6/2003 | Walak et al. | | | | |
| 2003/0114880 A1 | 6/2003 | Hansen et al. | | | | |
| 2003/0125790 A1 | 7/2003 | Fastovsky et al. | | | | |
| 2003/0125793 A1 | 7/2003 | Vesely | | | | |
| 2003/0130681 A1 | 7/2003 | Ungs | | | | |
| 2003/0144686 A1 | 7/2003 | Martinez et al. | | | | |
| 2003/0153943 A1 | 8/2003 | Michael et al. | | | | |
| 2003/0153945 A1 | 8/2003 | Patel et al. | | | | |
| 2003/0163159 A1 | 8/2003 | Patel et al. | | | | |
| 2003/0176888 A1 | 9/2003 | O'Connell | | | | |
| 2003/0181922 A1 | 9/2003 | Alferness | | | | |
| 2004/0010282 A1 | 1/2004 | Kusleika | | | | |
| 2004/0082966 A1 | 4/2004 | WasDyke | | | | |
| 2004/0158273 A1 | 8/2004 | Weaver et al. | | | | |
| 2004/0158274 A1 | 8/2004 | WasDyke | | | | |
| 2004/0186510 A1 | 9/2004 | Weaver | | | | |
| 2004/0193209 A1 | 9/2004 | Pavcnik et al. | | | | |
| 2004/0230220 A1 | 11/2004 | Osborne | | | | |
| 2005/0027314 A1* | 2/2005 | WasDyke ............ 606/200 | | | | |
| 2005/0159771 A1 | 7/2005 | Petersen | | | | |
| 2005/0165441 A1 | 7/2005 | McGuckin, Jr. et al. | | | | |
| 2005/0165442 A1 | 7/2005 | Thinnes, Jr. et al. | | | | |
| 2005/0251199 A1 | 11/2005 | Osborne et al. | | | | |
| 2005/0267512 A1 | 12/2005 | Osborne et al. | | | | |
| 2005/0267513 A1 | 12/2005 | Osborne et al. | | | | |
| 2005/0267514 A1* | 12/2005 | Osborne et al. ........ 606/200 | | | | |
| 2006/0030875 A1 | 2/2006 | Tessmer | | | | |

FOREIGN PATENT DOCUMENTS

| | | |
|---|---|---|
| DE | 3429850 A1 | 2/1986 |
| EP | 0270432 A1 | 6/1988 |
| EP | 0348295 A1 | 12/1989 |
| EP | 0350043 A1 | 10/1990 |
| EP | 0430848 A1 | 6/1991 |
| EP | 0437121 A2 | 7/1991 |
| EP | 0462008 A1 | 12/1991 |
| EP | 0472334 A1 | 2/1992 |
| EP | 0701800 A1 | 3/1996 |
| FR | 2587901 | 4/1987 |
| FR | 2649884 | 1/1991 |
| FR | 2672487 | 8/1992 |
| GB | 2200848 A | 8/1988 |
| GB | 2200848 B | 8/1988 |
| SU | 835447 | 6/1981 |
| SU | 1103868 A | 7/1984 |
| SU | 955912 A | 2/1988 |
| WO | WO 91/04716 | 4/1991 |
| WO | WO 91/11972 | 8/1991 |
| WO | WO 95/08567 | 3/1995 |
| WO | WO 95/27448 | 10/1995 |
| WO | WO 96/17634 | 6/1996 |
| WO | WO 01/06952 A1 | 2/2001 |
| WO | WO 03/011188 A1 | 2/2003 |
| WO | WO 2004/049973 A1 | 6/2004 |
| WO | WO 2005/072645 A1 | 8/2005 |
| WO | WO 2005/102210 A1 | 11/2005 |
| WO | WO 2005/102211 A1 | 11/2005 |
| WO | WO 2005/102212 A1 | 11/2005 |
| WO | WO 2005/102213 A1 | 11/2005 |
| WO | WO 2005/102214 A1 | 11/2005 |
| WO | WO 2006/036867 A1 | 4/2006 |

OTHER PUBLICATIONS

James Hansen, Metal That Remember, 44-47.
Morris Simon et al., Transvenous Devices for the Management of Pulmonary Embolism, 1980, 112-121.
J.L. Kraimps et al., Annals of Vascular Surgery, Mar. 1992, 99-110.
Jean-Louis Kraimps, M.D. et al., Optimal Central Trapping (OPCETRA) Vena Cava Filter: Results of Experimental Studies, Nov. 1992, 697-699.
International Search Report—PCT/US2005/013322 (Sep. 23, 2005).
International Search Report—PCT/US2005/013323 (Sep. 23, 2005).
International Search Report—PCT/US2005/013158 (Oct. 7, 2005).
International Search Report—PCT/US2005/013281 (Oct. 7, 2005).
International Search Report—PCT/US2005/013160) Sep. 22, 2005).
International Search Report—PCT/US2005/034350 (Feb. 10, 2006).
International Search Report—PCT/US2005/040299 (Apr. 11, 2007).

* cited by examiner

REMOVABLE VENA CAVA FILTER WITH IMPROVED LEG

BACKGROUND OF THE INVENTION

The present invention relates to medical devices. More particularly, the invention relates to a removable filter that can be percutaneously placed in and removed from a blood vessel, such as the vena cava, of a patient.

A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, filters generally have not been considered removable from a patient due to the likelihood of endotheliosis of the filter during treatment. After deployment of a filter in a patient, proliferating intimal cells begin to accumulate around the filter struts which contact the wall of the vessel. After a length of time, such ingrowth prevents removal of the filter without risk of trauma, requiring the filter to remain in the patient. As a result, there has been a need for an effective filter that can be removed after the underlying medical condition has passed.

In addition, further improvements may be made related to the delivery or retrieval of vena cava filters. It is desirable to lessen the scratching or scraping of the anchoring hooks against outer walls of an tube or a blood vessel while maintaining the effectiveness of the filter. For example, an anchoring feature should prevent migration toward the heart while allowing easy, non-traumatic removal when the patient's medical condition no longer exists. A vena cava filter can be subjected to considerable forces when the filter is substantially full of clot and the patient strains or performs a valsalva. This tends to dilate the vena cava and force a large volume of blood toward the heart. There have been incidences where filters designed for permanent implantation have been dislodged and migrated into the heart when confronted with such a challenge.

Thus, the anchoring hooks typically maintain the filter in place by penetrating the vessel wall. However, anchoring hooks also may scrape or scratch the blood vessel during delivery or retrieval.

BRIEF SUMMARY OF THE INVENTION

The present invention provides a removable filter for capturing thrombi in a blood vessel. The removable filter has primary struts having anchoring hooks at free ends to engage the vessel wall. On at least one of the primary struts, a resistant portion is disposed next to the anchoring hook. The primary struts exert pressure on the vessel wall when the filter is deployed. In a given strut, some of that pressure is exerted through the resistant portion and some is exerted through the anchoring hook. This results in the anchoring hook penetrating the vessel less deeply, as some of the pressure exerted on the vessel wall by the primary strut is exerted through the resistant portion, instead of all of the pressure of the primary strut being exerted through the anchoring hook.

In one example, the present invention provides a removable filter having a plurality of primary struts, the primary struts having first ends attached together along a longitudinal axis of the filter. Each primary strut has a body member extending from the first end along the longitudinal axis to an anchoring hook. Each primary strut is configured to move relative to the longitudinal axis between an expanded state for engaging with the blood vessel and a collapsed state for filter delivery or retrieval. At least one primary strut has a resistant portion proximate the anchoring hook. The resistant portion is configured to contact the blood vessel in the expanded state. The removable filter also has a plurality of secondary struts. The secondary struts have proximal ends attached together along the longitudinal axis and distal ends located radially from the longitudinal axis in the expanded state. The plurality of secondary struts is configured to engage the blood vessel to centralize the filter in the expanded state in the blood vessel.

In another example, the present invention provides another variation of a removable filter for capturing thrombi in a blood vessel. The filter includes a plurality of primary struts having first ends attached together along a longitudinal axis of the filter. Each primary strut has a body member extending from the first end along the longitudinal axis to an anchoring hook. In addition, each primary strut is configured to move relative to the longitudinal axis between an expanded state for engaging with the blood vessel and a collapsed state for filter delivery or retrieval. At least one primary strut has a bend proximate the anchoring hook. The bend is configured to contact the blood vessel in the expanded state. The filter also has a plurality of secondary struts having proximal ends attached together along the longitudinal axis and distal ends located radially from the longitudinal axis in the expanded state. The secondary struts are configured to engage the blood vessel to centralize the filter in the expanded state in the blood vessel.

In yet another example, the present invention provides another variation of a removable filter for capturing thrombi in a blood vessel. The filter includes a plurality of primary struts having first ends attached together along a longitudinal axis of the filter. Each primary strut has a body member extending from the first end along the longitudinal axis to an anchoring hook. Each primary strut is configured to move relative to the longitudinal axis between an expanded state for engaging with the blood vessel and a collapsed state for filter delivery or retrieval. At least one primary strut has a flattened portion proximate the anchoring hook. The flattened portion is configured to contact the blood vessel in the expanded state. The filter also has a plurality of secondary struts with proximal ends attached together along the longitudinal axis and distal ends located radially from the longitudinal axis in the expanded state. The secondary struts are configured to engage the blood vessel to centralize the filter in the expanded state in the blood vessel.

In still another example, the present invention provides another variation of a removable filter for capturing thrombi in a blood vessel. The filter has a plurality of primary struts having first ends attached together along a longitudinal axis of the filter. Each primary strut has a body member extending from the first end along the longitudinal axis to an anchoring hook. Each primary strut is configured to move relative to the longitudinal axis between an expanded state for engaging with the blood vessel and a collapsed state for filter delivery or retrieval. At least one primary strut has a marker band proximate the anchoring hook. The marker band is configured to contact the blood vessel in the expanded state. The filter also has a plurality of secondary struts having proximal ends attached together along the longitudinal axis and distal ends located radially from the longitudinal axis in the expanded state. The plurality of secondary struts is configured to engage the blood vessel to centralize the filter in the expanded state in the blood vessel.

In another variation, the present invention provides a removable filter assembly for capturing thrombi in a blood vessel. The assembly includes a removable filter and a tube. The removable filter has a plurality of primary struts having first ends attached together along a longitudinal axis of the filter. Each primary strut has a body member extending from the first end along the longitudinal axis to an anchoring hook, and each primary strut is configured to move relative to the longitudinal axis between an expanded state for engaging with the blood vessel and a collapsed state for filter delivery or retrieval. At least one primary strut has a resistant portion proximate the anchoring hook. The resistant portion is configured to contact the blood vessel in the expanded state. The filter also has a plurality of secondary struts having proximal ends attached together along the longitudinal axis and distal ends located radially from the longitudinal axis in the expanded state. The plurality of secondary struts is configured to engage the blood vessel to centralize the filter in the expanded state in the blood vessel. Further, the filter has a hub configured to axially house the first ends of the plurality of primary struts and a retrieval hook extending from the hub opposite the plurality of primary struts for removal of the filter from the blood vessel. The removable filter is disposed in the tube in the collapsed state for retrieval or delivery of the filter.

Further aspects, features, and advantages of the invention will become apparent from consideration of the following description and the appended claims when taken in connection with the accompanying drawings.

BRIEF DESCRIPTION OF THE DRAWINGS

FIG. 2D-1 is a cross-sectional view of the vena cava in which the filter of FIG. 2D has been deployed, in accordance with the principles of the present invention;

DETAILED DESCRIPTION OF THE INVENTION

Figure 1:
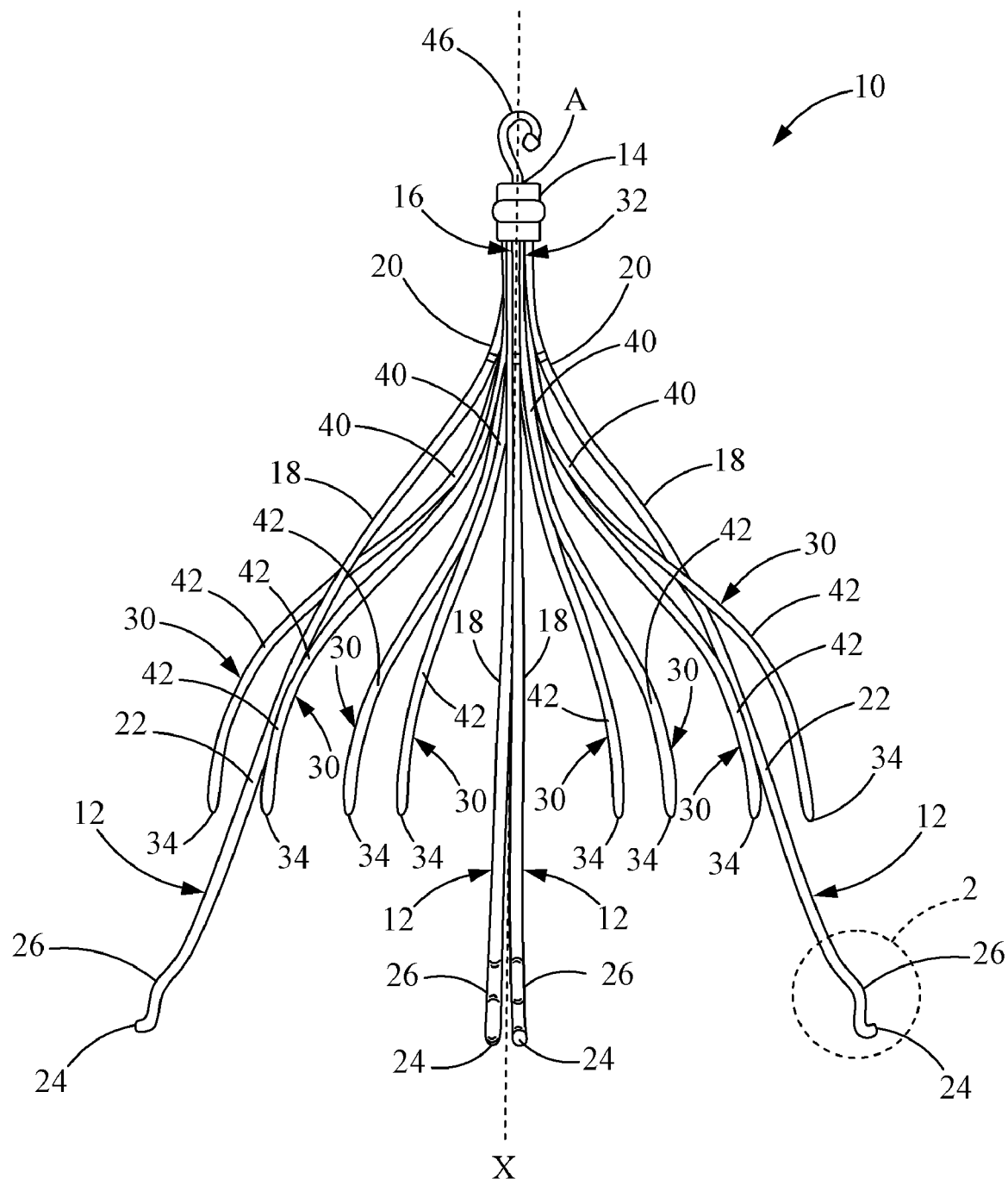
FIG. 1 is a side perspective view of a vena cava filter in an expanded state, according to the principles of the present invention.

Referring now to FIG. 1, a vena cava filter 10 is illustrated in an expanded state. The vena cava filter 10 may be implanted within a blood vessel, such as a vena cava, for the purpose of lysing or capturing thrombi carried by the blood flowing through the iliac veins toward the heart and into the pulmonary arteries. The vena cava filter 10 may be percutaneously deployed through the femoral vein, by way of example. Preferably, the vena cava filter 10 has a length smaller than the length of the inferior vena cava. It should be understood that the filter 10 may also be used as a filter within other blood vessels or body vessels, without falling beyond the spirit and scope of the present invention.

As illustrated in FIG. 1, the vena cava filter 10 comprises four primary struts 12 each having first ends 16 that emanate from a hub 14. The hub 14 attaches the primary struts 12 by crimping the first ends 16 of the primary struts 12 together at a center point A in a compact bundle to define a central or longitudinal axis X of the filter 10. It should be understood that the use of four primary struts 12 is merely one variation of the present invention, and a greater or fewer number of primary struts 12 could be employed, without falling beyond the spirit and scope of the present invention.

Preferably, the primary struts 12 are formed from superelastic material, stainless steel wire, cobalt-chromium-nickel-molybdenum-iron alloy, Nitinol, radiopaque Nitinol, titanium, cobalt-chrome alloy, thermosetting and thermoplastic polymers, or any suitable material that will result in a self-opening or self-expanding filter. In this embodiment, the primary struts 12 are preferably formed from wire having a round or near round cross-section with a diameter of at least about 0.015 inches. However, it is not necessary that the primary struts 12 have a round cross-section. For example, the primary struts 12 could take on any shape to maintain a non-turbulent blood flow therethrough. In some embodiments, the primary struts 12 could be formed of a flat wire.

Each primary strut 12 includes a body member 18. In this embodiment, the body member 18 is an arcuate segment having a soft S-shape in an expanded state. In the expanded state, each body member 18 is formed with a first curved portion 20 that is configured to softly bend away from the longitudinal or central axis X of the filter 10 and a second curved portion 22 that is configured to softly bend toward the longitudinal axis X of the filter 10. For each primary strut 12, the body member 18 extends from the first end 16 along the longitudinal axis X to a resistant portion 26 and an anchoring hook 24. The first curved portion 20 extends from the first end 16, and the second curved portion 22 extends from the first curved portion 20 to the resistant portion 26, which is adjacent the anchoring hook 24.

The primary struts 12 radially extend from the first ends 16. In this embodiment, the primary struts 12 extend linearly radially in the expanded state to avoid entanglement with other struts. In other words, each primary strut 12 contacts the other primary struts 12 only at the hub 14 in the expanded state. The first curved portion 20 is configured to curve away from the longitudinal axis X of the filter 10, such that the slope of the first curved portion 20 increases along the path of the first curved portion 20 with respect to the longitudinal axis X, starting from the hub 14 and moving along the first curved portion 20. The second curved portion 20 is configured to curve radially toward the longitudinal axis X in the expanded state, such that the slope of the second curved portion decreases along the path of the second curved portion 22 with respect to the longitudinal axis X, starting from the first curved portion 20 and moving along the path of the second curved portion 22. A point of inflection separates the first curved portion 20 from the second curved portion 22, where the slope changes direction, that is, where the slope stops increasing with respect to the longitudinal axis X, just before the slope begins to decrease with respect to the longitudinal axis X. In other words, the first curved portion 20 is concave, and the second curved portion of convex, when viewed from the side.

Each primary strut 12 terminates at the anchoring hook 24. In this embodiment, each primary strut 12 has only a single anchoring hook 24. The anchoring hooks 24 will anchor in the vessel wall when the filter 10 is deployed at a delivery location in the blood vessel. Each anchoring hook 24 has a constant angle with respect to the longitudinal axis X.

The anchoring hooks 24 prevent the filter 10 from migrating from the delivery location in the blood vessel where it has been deposited. When the filter 10 is deployed in a blood vessel, the anchoring hooks 24 engage the walls of the blood vessel to define a first axial portion to secure the filter in the blood vessel. To prevent the anchoring hooks 24 from penetrating the vessel wall deeply, and thus to lessen the trauma suffered by the vessel wall, the body members 18 include resistant portions 26 disposed proximate to the anchoring hooks 24. In the present embodiment, each body member 18 has a resistant portion 26 proximate an anchoring hook 24; however, it should be understood that in other embodiments, only one of the body members 18 (a single body member 18) may have a resistant portion 26. The resistant portion 26 is configured to contact the blood vessel in the expanded state, which is described in further detail below.

Each primary strut 12 is flexible and configured to move relative to the longitudinal axis X between an expanded state for engaging the anchoring hooks 24 with the blood vessel and a collapsed state for filter retrieval or delivery.

The primary struts 12 are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm when freely expanded. The primary struts 12 have sufficient spring strength such that when the filter 10 is deployed the anchoring hooks 24 will anchor into the vessel wall.

In this embodiment, the filter 10 includes a plurality of secondary struts 30 having proximal ends 32 that also emanate from hub 14. The hub 14 attaches by crimping the connected proximal ends 32 at the center point A of the secondary struts 30 together with the primary struts 12. In this embodiment, each primary strut 12 has two secondary struts 30 in side-by-side relationship with the primary strut 12. The secondary struts 30 extend from the connected proximal ends 32 to free distal ends 34 to centralize the filter 10 in the expanded state in the blood vessel. As shown, each secondary strut 30 extends arcuately along the longitudinal axis and linearly radially from the proximal end 32 to the distal end 34, the distal end 34 being a free end. Thus, the distal ends 34 are located radially from the longitudinal axis X in the expanded state. As with the primary struts 12, the secondary struts 30 extend linearly radially and avoid entanglement with other struts.

The secondary struts 30 may be made from the same type of material as the primary struts 12. However, in some embodiments, the secondary struts 30 may have a smaller diameter, e.g., at least about 0.012 inches, than the primary struts 12. As shown, two secondary struts 30 are disposed on each side of one primary strut 12 to form a part of a netting configuration of the filter 10.

In this embodiment, each of the secondary struts 30 is formed of a first arc 40 and a second arc 42. The first arc 40 extends from the connected proximal end 32 away from the longitudinal axis X. The second arc 42 extends from the first arc 40 to the distal end 34, toward the longitudinal axis X. In other words, the first arc 40 is concave and the second arc 42 is convex when viewed from the side. Put another way, the first arc 40 has a slope that increases along the path of the first arc 40 with respect to the longitudinal axis X, starting at the hub 14 and moving along the path of the first arc 40; and, the second arc 42 has a slope that decreases along the path of the second arc 42 with respect to the longitudinal axis X, starting at the hub 14 and moving along the path of the second arc 42.

In this embodiment, the hub 14 is preferably made of the same material as the primary and secondary struts 12, 30 to reduce the possibility of galvanic corrosion or molecular changes in the material due to welding. The hub 14 forms a sleeve that axially houses the first ends 16 of the primary struts 12 and the proximal ends 32 of the secondary struts 30. As shown, a retrieval hook 46 extends from hub 14 opposite the primary and secondary struts 12, 30 for removal of the filter 10 from the blood vessel.

When freely expanded, the free distal ends 34 of the secondary struts 30 will expand radially outwardly to a diameter of about 25 mm to 45 mm, in this embodiment, to engage the vessel wall. For example, the secondary struts 30 may expand radially outwardly to a diameter of between about 35 mm and 45 mm. The second arcs 42 engage the wall of a blood vessel at the distal ends 34 to define a second axial portion where the vessel wall is engaged. The secondary struts 30 function to stabilize the position of the filter 10 about the center of the blood vessel in which it is deployed. As a result, the filter 10 has two layers or portions of struts 12, 30 longitudinally engaging the vessel wall of the blood vessel.

The spring biased configuration of the primary struts 12 further causes the anchoring hooks 24 to engage the vessel wall and anchor the filter at the location of deployment. After initial deployment, the pressure of the blood flow on the filter 10 contributes in maintaining the anchoring hooks 24 anchored in the inner lining of the inferior vena cava, or other blood vessel in which the filter 10 is deployed. The second arcs 42 of secondary struts 30 also have a spring biased configuration to engage with the vessel wall.

The length of the filter 10 is preferably defined by the length of a primary strut 12. Furthermore, the diameter of the hub 14 is defined by the size of a bundle containing the primary struts 12 and secondary struts 30. In this embodiment, the eight secondary struts 30 minimally add to the diameter of the hub 14, due to the reduced diameter of each secondary strut 30. This is accomplished while maintaining the filter 10 in a centered attitude relative to the vessel wall and formed as a part of the netting configuration of the filter 10.

In this embodiment, each body member 18 has a thickness of at least about 0.015 inch and an ultimate tensile strength of between about 285,000 pounds per square inch (psi) and 330,000 psi. Each anchoring hook 24 is integral with the body member 18 to which it is attached and has the same thickness and ultimate tensile strength as the body member 18. Each secondary strut 30 has a thickness of at least about 0.012 inch and an ultimate tensile strength of between about 285,000 psi and 330,000 psi.

Figure 2:
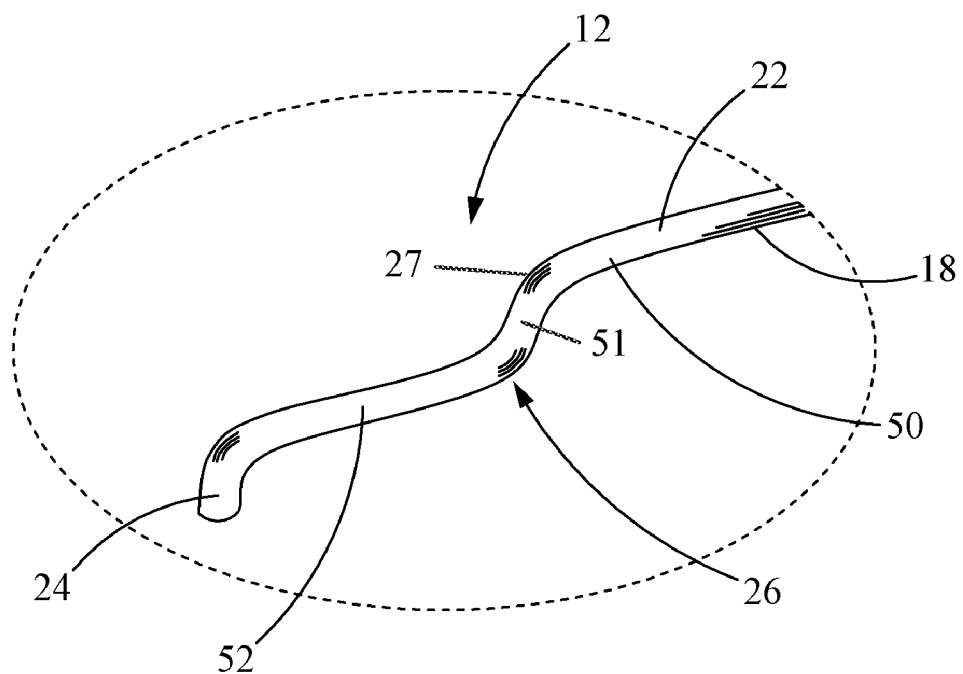
FIG. 2 is an enlarged perspective view of a portion of the vena cava filter of FIG. 1, depicting a portion of a primary strut in circle 2.

Now with reference to FIG. 2, a portion of the body member 18 of the primary strut 12 is shown. In this embodiment, the resistant portion 26 is a bend disposed next to the anchoring hook 24. The bend 26 has a radius of curvature that is smaller than the radius of curvature of the second curved portion 22 of the body member 18. The bend 26 is configured to contact the vessel wall when the filter 10 is deployed in a body vessel in the expanded state and apply pressure to the blood vessel at the bend 26 to decrease the pressure applied to the blood vessel by the anchoring hook 24. Thus, some of the spring force exerted on the vessel wall by the primary strut 12 is exerted at the bend 26. Some of the spring force of the primary strut 12 is also exerted on the vessel wall by the anchoring hook 24, resulting in the anchoring hook 24 holding the filter 10 in place within the body vessel.

In this embodiment, the first bend 26 and second bend 27 separate two approximately parallel portions 50, 52 of the body member 18. In other words, a proximal portion 50 is disposed at the end of the second curved portion 22, and the first and second bends 26 and 27 separate the proximal portion 50 from the distal portion 52 connected to the anchoring hook 24. The body member 18 is configured to extend from each side of the first bend 26. A first side 51 of the body member 18 is configured to extend from the first bend 26 away from the vessel wall in the expanded state. A distal portion (or second side) 52 of the body member 18 is configured to extend from the first bend 26 to the anchoring hook 24 parallel to the vessel wall in the expanded state. Thus, when the filter 10 is deployed within a body vessel, both the first bend 26 and the anchoring hook 24 contact the vessel wall and exert pressure thereon, and the anchoring hook 24 mildly penetrates the vessel wall. The penetration is lessened because of the force exerted on the vessel wall by the bend 26. In this embodiment, the bend 26, the distal portion 52, and the anchoring hook 24 each remain in contact with the blood vessel when the filter 10 is deployed within a blood vessel in the expanded state.

Figure 2A:
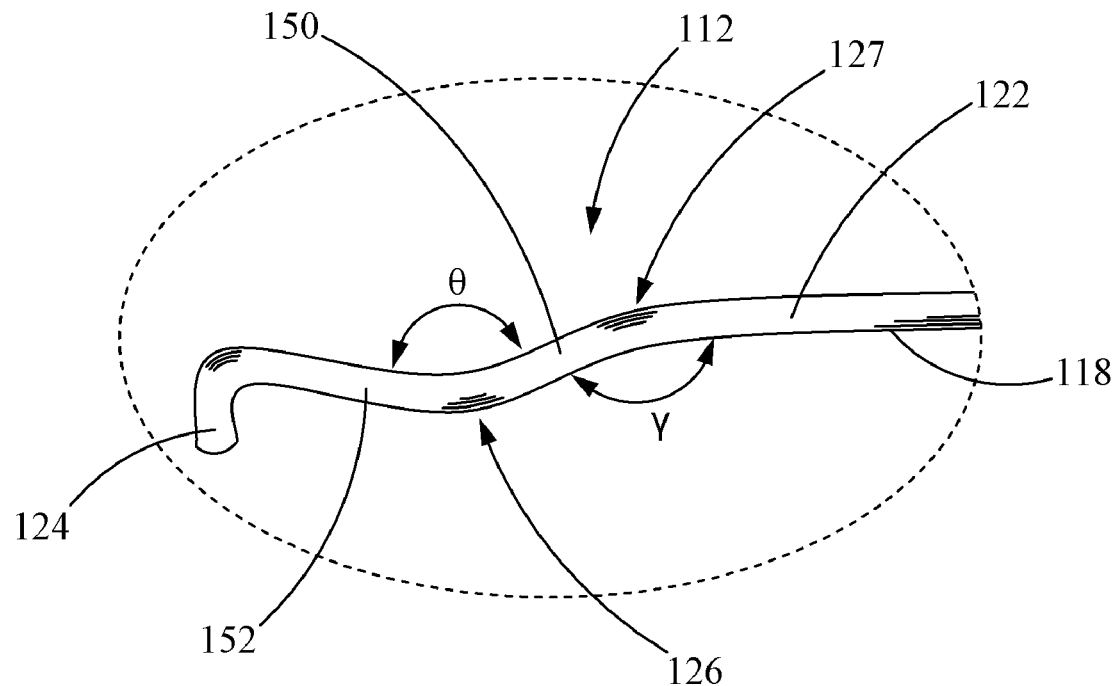
FIG. 2A is an enlarged perspective view of a portion of another primary strut of a vena cava filter in circle 2A, according to the principles of the present invention.

Now with reference to FIG. 2A, another embodiment of a primary strut 112 is illustrated. It should be understood that the primary strut 112 could be part of the filter 10, the filter 10 also having secondary struts 30 as shown and described with reference to FIG. 1. The primary strut 112 could have first and second curved portions, similar to the first and second curved portions 20, 22 described with reference to FIG. 1. In this embodiment, the second curved portion is referred to with the numeral 122.

In the embodiment of FIG. 2A, the primary strut 112 has a body member 118, which terminates in an anchoring hook 124. A bend 126 is formed in the body member 118 proximate the anchoring hook 124. Proximal and distal portions 150, 152 extend from each side of the bend 126. In other words, the body member 118 is configured to extend from each side of the bend 126 away from the blood vessel in the expanded state (when deployed in the blood vessel). Thus, in the expanded state, the anchoring hook 124 and the bend 126 contact the vessel wall when the filter 10 is deployed within a blood vessel, however, the distal portion 152 may extend away from the vessel wall. In other words, in some embodiments, the distal portion 152 may not contact the vessel wall in the expanded state when deployed.

Similarly to the body member 18 of FIG. 2, the body member 118 of FIG. 2A is configured such that the bend 126 applies pressure on the blood vessel to decrease the amount of pressure applied to the blood vessel by the anchoring hook 124. In other words, the body member 118 exerts a spring force on the blood vessel, part of which is applied through the bend 126 and part of which is applied through the anchoring hook 124. In this way, the anchoring hook 124 penetrates the blood vessel less deeply than it would if the bend 126 did not also exert part of the spring force of the body member 118 on the vessel wall, for example, if the body member 118 was lacking the bend 126.

In some variations of the primary strut 112, the bend 126 has an angle of inclusion θ in the range of about 135° to about 155°, and preferably about 145°. In other words, the proximal portion 150 extends from the distal portion 152 at an angle θ in the range of about 135° to about 155° with respect to the distal portion 152 at the point of the bend 126, with the bend 126 separating the proximal and distal portions 150, 152.

Furthermore, in some embodiments, such as the one pictured in FIG. 2A, the proximal portion 150 extending from the bend 126 may be connected to the second curved portion 122 of the body member 118 with a second bend 127, the second bend 127 having an angle of inclusion γ in the range of about 150° to about 170° degrees, preferably about 160°. In other words, the proximal portion 150 extends from the second curved portion 122 at an angle γ in the range of about 150° to about 170° with respect to the second curved portion 122 at the point of the second bend 127, with the second bend 127 separating the second curved portion 122 and the proximal portion 150.

It should be understood that other angles of inclusion θ, γ could be used, without falling beyond the spirit and scope of present invention. The range given above includes merely some of the embodiments within the spirit and scope of the present invention.

Figure 2B:
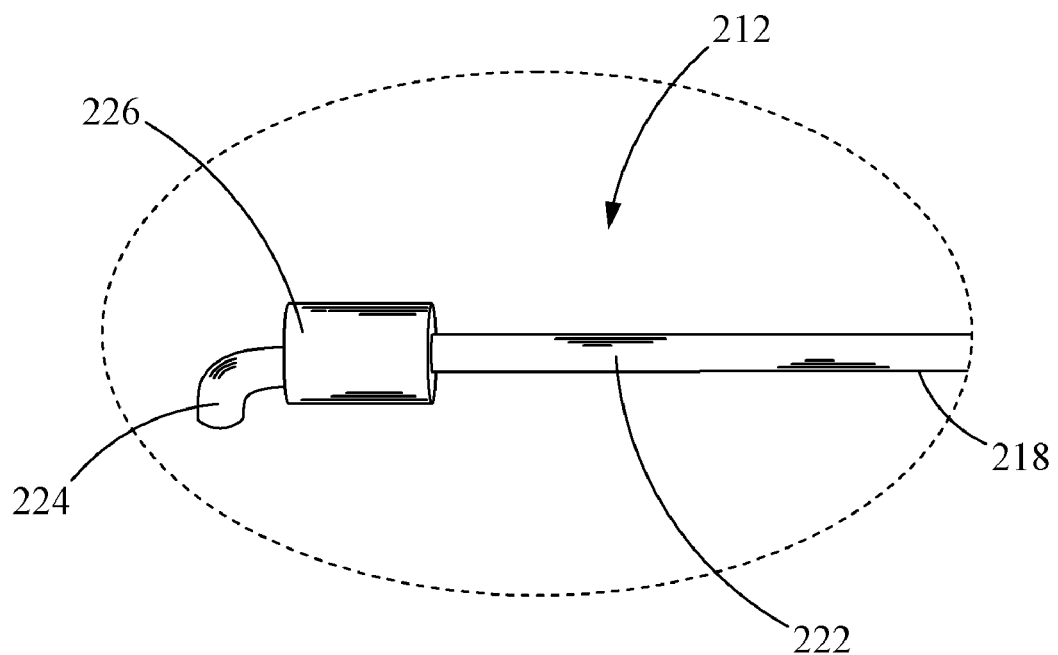
FIG. 2B is an enlarged perspective view of a portion of yet another primary strut of a vena cava filter in circle 2B, in accordance with the principles of the present invention.

Now with reference to FIG. 2B, another variation of a portion of a primary strut 212 for use with the filter 10 is illustrated. The primary strut 212 may be used with the filter 10, such that the filter 10 includes secondary struts 30, a hub 14, and a hook 46 as hereinbefore described. Further, the primary strut 212 may be similar to the primary strut 12 of FIG. 1; for example, the primary strut 212 may have a first curved portion 20 and a second curved portion 22 as hereinbefore described. In this embodiment, the second curved portion is referred to with the numeral 222.

In this embodiment, the primary strut 212 has a body member 218 including a resistant portion in the form of a marker band 226 disposed proximate the anchoring hook 224. The marker band 226 is disposed at the distal end of the second curved portion 222 of the body member 218, between the distal end of the second curved portion 222 and the anchoring hook 224, wherein the distal end of the second curved portion 222 is defined as the end of the second curved portion 222 farthest from the hub 14.

The marker band 226 may be used for viewing the filter 10 by fluoroscopy, as is known in the art. Although shown as being cylindrical, the marker band 226 may be of any other suitable shape, such as an oval shape or ellipsoid shape, without falling beyond the spirit and scope of the present invention.

When the filter 10 is deployed in the body vessel in the expanded state, the body member 218 is configured such that marker band 226 contacts the vessel wall and the anchoring hook 224 engages the vessel wall. The filter 10 is preferably self-expanding, and the body member 218 exerts a spring force on the vessel wall. Part of that spring force is exerted by the marker band 226 and part of that spring force is exerted by the anchoring hook 224. Other portions of the primary strut 212 may also exert a spring force on the vessel wall, without falling beyond the spirit and scope of the present invention. Thus, both the marker band 226 and the anchoring hook 224 apply pressure on the vessel wall. Because a portion of the spring force of the body member 218 is exerted through the marker band 226, the amount of force exerted by the anchoring hook 224 is lessened. The result is that the anchoring hook 224 penetrates the vessel wall less deeply than it would if the marker band 226 did not apply a force to the vessel wall, in this embodiment.

Figure 2C:
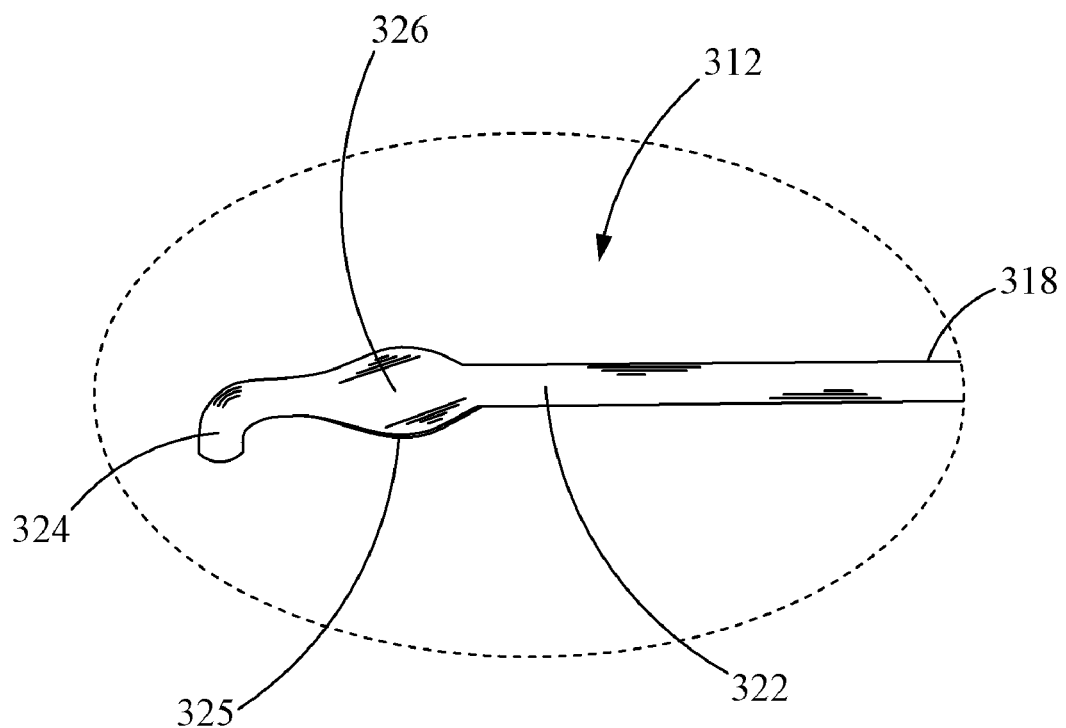
FIG. 2C is an enlarged perspective view of a portion of still another primary strut of a vena cava filter in circle 2C, according to the principles of the present invention.

Referring now to FIG. 2C, yet another variation of a primary strut 312 for use with the filter 10 is illustrated. Like the previous embodiments, it should be understood that the filter 10 could have secondary struts 30, a hub 14, and a retrieval hook 46 as previously described. Furthermore, the primary strut 312 could have a first curved portion 20 and a second curved portion 22; the second curved portion will be referred to with the numeral 322 in this embodiment.

The primary strut 312 has a body member 318 including a resistant portion 326 at the distal end of the second curved portion 322, the distal end of the second curved portion 322 being defined as the end of the second curved portion 322 that is farthest from the hub 14. In this embodiment, the resistant portion 326 is a flattened portion 326, and it is disposed adjacent an anchoring hook 324. The anchoring hook 324 is disposed at the free end of the body member 318. The flattened portion 326 may be formed by flattening out or smashing a portion of the body member 318 that is adjacent the anchoring hook 324. If the body member 318 is a round metallic wire, a portion of that wire may be pinched near the anchoring hook 324 to form the flattened portion 326, for example, by pinching the wire with a tool.

When the filter 10 is deployed in the body vessel in the expanded state, the body member 318 is configured such that the outer edge 325 of the flattened portion 326 contacts the vessel wall and the anchoring hook 324 engages the vessel wall. The filter 10 is preferably self-expanding, and the body member 318 exerts a spring force on the vessel wall. Part of that spring force is exerted by the flattened portion 326 and part of that spring force is exerted by the anchoring hook 324. Other portions of the primary strut 312 may also exert a spring force on the vessel wall, without falling beyond the spirit and scope of the present invention. Thus, both the flattened portion 326 and the anchoring hook 324 apply pressure on the vessel wall. Because a portion of the spring force of the body member 318 is exerted through the flattened portion 326, the amount of force exerted by the anchoring hook 324 is lessened. The result is that the anchoring hook 324 penetrates the vessel wall less deeply than it would if the there was no flattened portion 326 in this embodiment, or if the flattened portion 326 did not apply a force to the vessel wall in this embodiment.

Figure 2D:
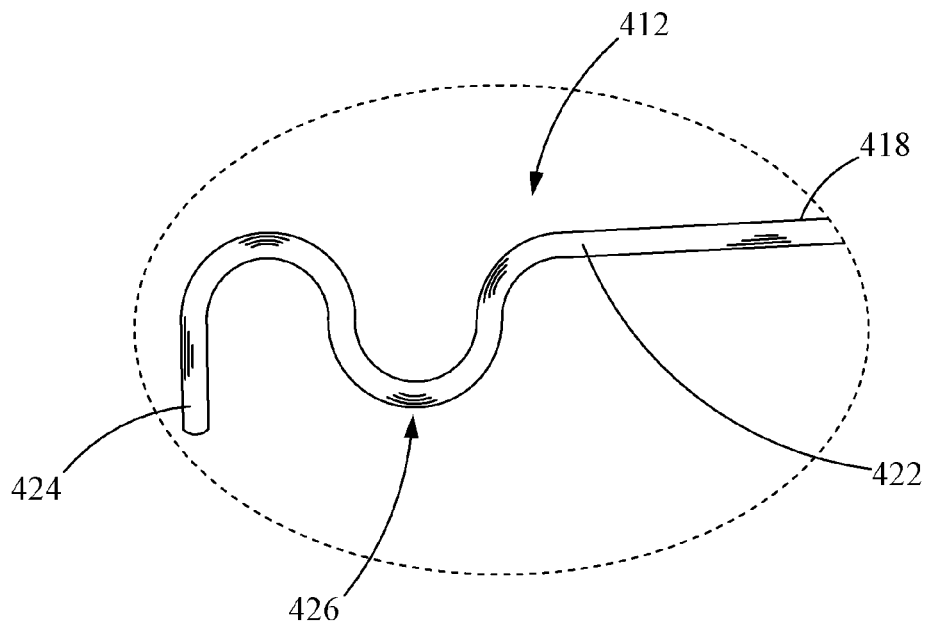
FIG. 2D is an enlarged perspective view of a portion of still another primary strut of a vena cava filter in circle 2D, according to the principles of the present invention.
Figures 1, 2D:
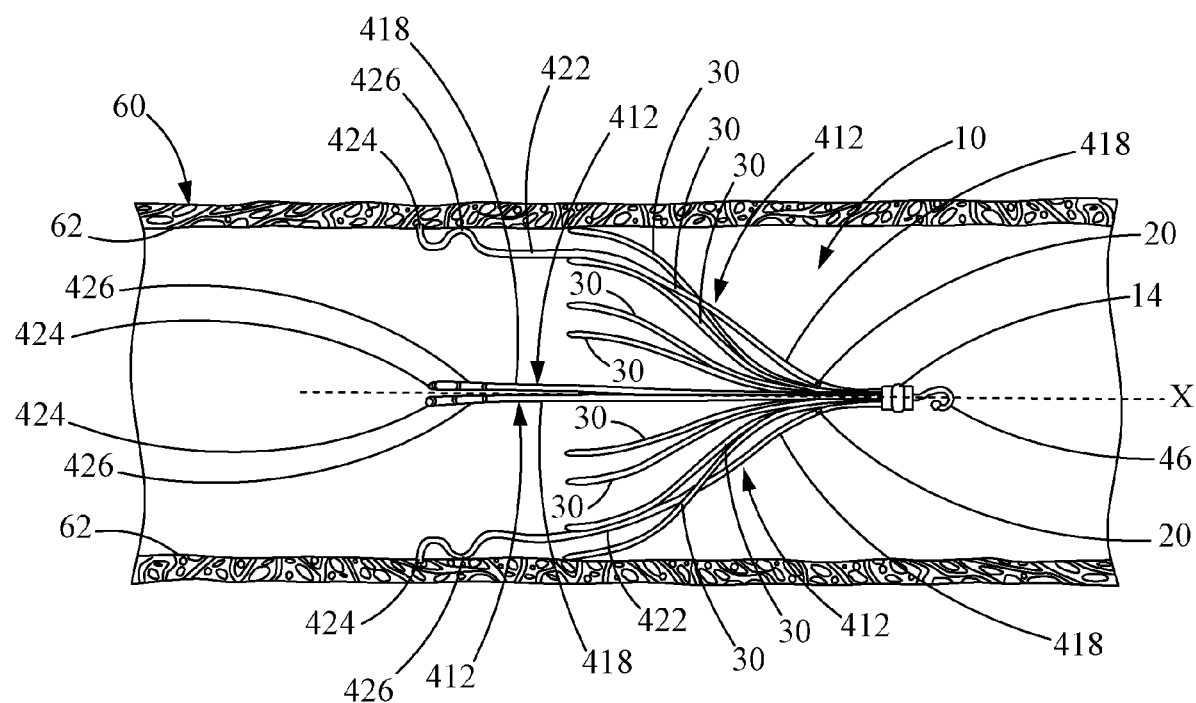

Referring now to FIG. 2D, yet another variation of a primary strut 412 for use with the filter 10 is illustrated. The filter 10 may be similar to the filter 10 of FIG. 1, for example, the filter 10 may have secondary struts 30, a hub 14, and a retrieval hook 46 as described above. Furthermore, the primary strut 412 has a body member 418 having a first curved portion 20 and a second curved portion 422, the second curved portion 422 being disposed adjacent a resistant portion 426. The resistant portion 426 is disposed proximate an anchoring hook 424, which is disposed at a free end of the body member 418.

In this variation, the resistant portion 426 is arcuate in shape, and further, it is semicircular in this embodiment. When the filter 10 is deployed in a blood vessel in the expanded state, the outer side of the arc of the resistant portion 426 contacts the vessel wall. In the expanded state, the body member 418 exerts a spring force on the vessel wall when deployed in a body vessel. Pressure is applied to the vessel wall by both the resistant portion 426 and the anchoring hook 424. Thus, a portion of the spring force exerted by the body member 418 is exerted through the resistant portion 426 and a portion of the spring force exerted by the body member 418 is exerted through the anchoring hook 424. The fact that the resistant portion exerts a spring force on the vessel wall, in addition to the anchoring hook 424 doing so, decreases the amount of force that the anchoring hook 424 exerts on the vessel wall. The result is that the anchoring hook 424 penetrates the vessel wall less deeply than it would if the resistant portion 426 was not present or did not exert a force on the vessel wall. It should be understood that other portions of the body member 418 could also exert a force on the vessel wall, without falling beyond the spirit and scope of the present invention.

As discussed above, the resistant portion 426 has an arcuate shape. The resistant portion 426, thus, has a bend radius, which is the radius of the resistant portion 426, or the radius of the arc of the resistant portion 426. Further, the second curved portion 422 of the body member 418 has an arcuate shape, and the radius of the arc of the second curved portion 422 may be referred to as the body member arc radius. As can be seen from the drawings, the bend radius is smaller than the body member arc radius. In other words, the second curved portion 422 forms a larger arc than the arc of the resistant portion 426. Thus, the bend radius is distinguished from the body member arc radius, and the resistant portion 426 is distinguished from the second curved portion 422. In some embodiments, the bend radius is more than twice as small as the body member arc radius. Further, in some embodiments, the bend radius is more than three times as small as the body member arc radius.

Now with reference to FIG. 2D-1, the filter 10 is shown deployed within a body vessel 60 in the expanded state. The filter 10 has a hub 14, a retrieval hook 46, and secondary struts 30 configured to centralize the filter 10 within the body vessel 60. The filter 10 of FIG. 2D has four primary struts 412 of the type illustrated in FIG. 2D. Thus, the primary struts 412 have body portions 418 having a first curved portion 20 connected to a second curved portion 422, wherein a resistant portion 426 is disposed at the distal end of the second curved portion 422 and adjacent to an anchoring hook 424, the distal end of the second curved portion 422 being defined as the end of the second curved portion 422 that is disposed farthest from the hub 14.

The body members 418 exert a force on the vessel wall 62 through the anchoring hooks 424 and the resistant portions 426. The body members 418 are preferably self-expanding, but they may also be expanded through heating or cooling. The anchoring hooks 424 penetrate the vessel wall 62 to anchor the filter 10 within the blood vessel 60, so that the filter 10 does not migrate once deployed. The resistant portions 426 apply some of the force of the body members 418 so that the force that the anchoring hooks 424 exert on the vessel wall 62 is decreased. In this way, the anchoring hooks 424 penetrate into the vessel wall 62 less deeply than they would if the resistant portions 426 were not exerting pressure or force on the vessel wall 62. With the anchoring hooks 424 penetrating less deeply into the vessel wall 62, they may be more easily removed, and/or removed with less scraping, tearing, or scarring.

Figure 3:
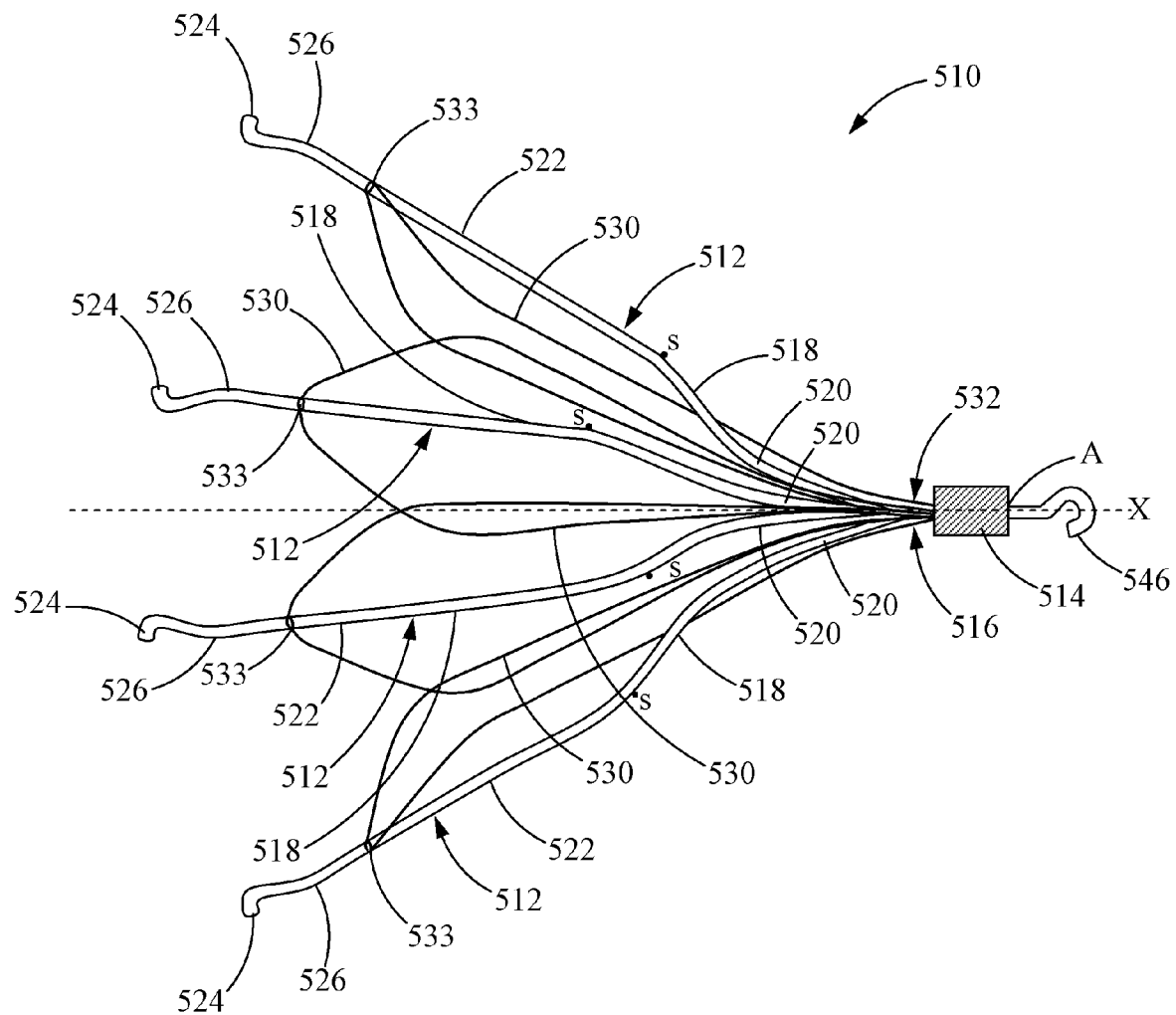
FIG. 3 is a side perspective view of still another vena cava filter in an expanded state, according to the principles of the present invention.

Now with reference to FIG. 3, another example of a filter 510 within the spirit and scope of the present invention is illustrated. Similarly to the filter 10 of FIG. 1, the filter 510 of FIG. 3 has four spring-biased expandable primary struts 512, each having first ends 516 that emanate from a common, central hub 514. The hub 514 may attach the primary struts 512 by crimping the first ends 516 of the primary struts 512 together at a center point A in a compact bundle to define a central or longitudinal axis X of the filter 510. The primary struts 512 could be of similar shapes, sizes, materials, and ultimate tensile strengths as those described above with reference to FIG. 1.

Each primary strut 512 includes a body member 518. In this embodiment, the body member 518 includes an arcuate segment 520 that extends in a curved shape outward from the hub 514 and outward from a longitudinal axis X defined by the center of the filter 510 and the attached together ends 516, in an expanded state. The body member 518 further comprises a straight portion 522 that is connected to the arcuate segment 520 at a shoulder point S. The straight portion 522 is connected to a resistant portion 526, which is further connected to an anchoring hook 524. Each anchoring hook 524 has a constant angle with respect to the longitudinal axis X. The resistant portion 526 and the anchoring hook 524 work together as described above to apply a force to the vessel wall of a body vessel, such that the anchoring hook 524 is not responsible for applying all of the spring force of the body member 518 on the vessel wall. The result is that the anchoring hook 526 penetrates the vessel wall less deeply than it would if the resistant portion 526 did not also apply part of the spring force of the body member 518 to the vessel wall. The anchoring hooks 524 prevent the filter 510 from migrating within the blood vessel.

Each primary strut 512 is flexible and configured to move relative to the longitudinal axis X between an expanded state for engaging the anchoring hooks 524 with the blood vessel and a collapsed state for filter 510 retrieval or delivery.

The primary struts 512 radially extend from the first ends 516. Like the embodiment of FIG. 1, in this embodiment, the primary struts 512 extend linearly radially in the expanded state to avoid entanglement with other primary struts 512. In other words, each primary strut 512 contacts the other primary struts 512 only at the hub 514 in the expanded state.

In this embodiment, the filter 510 includes four secondary struts 530 having proximal ends 532 that also emanate from the hub 514. The proximal ends 532 are attached together at the hub 514. Middle portions 533 of the secondary struts 530 are wrapped around the primary struts 512. In this embodiment, the middle portions 533 are wrapped around the straight portions 522 of the primary struts 512; however, it should be understood that the secondary struts 530 could be wrapped around, or otherwise attached, to other parts of the primary struts 512 without falling beyond the spirit and scope of the present invention. The secondary struts 530 help centralize the filter 510 when it is deployed in a body vessel in the expanded state.

Furthermore, it should be understood that the primary and secondary struts 12, 30, 512, 530 described herein could have other configurations without falling beyond the spirit and scope of the present invention. One such variation could include using the primary struts 512 as described with respect to FIG. 3 and the secondary struts 30 as described with respect to FIG. 1.

The secondary struts 530 may be made from the same type of material as the primary struts 512. However, in some embodiments, the secondary struts 530 may have a smaller diameter than the primary struts 512. In this embodiment, the hub 514 is preferably made of the same material as the primary and secondary struts 512, 530 to reduce the possibility of galvanic corrosion or molecular changes in the material due to welding. The hub 514 forms a sleeve that axially houses the first ends 516 of the primary struts 512 and both ends 532 of the secondary struts 530. As shown, a retrieval hook 546 extends from hub 514 opposite primary and secondary struts 512, 530 for removal of the filter 510 from the blood vessel.

Figure 4:
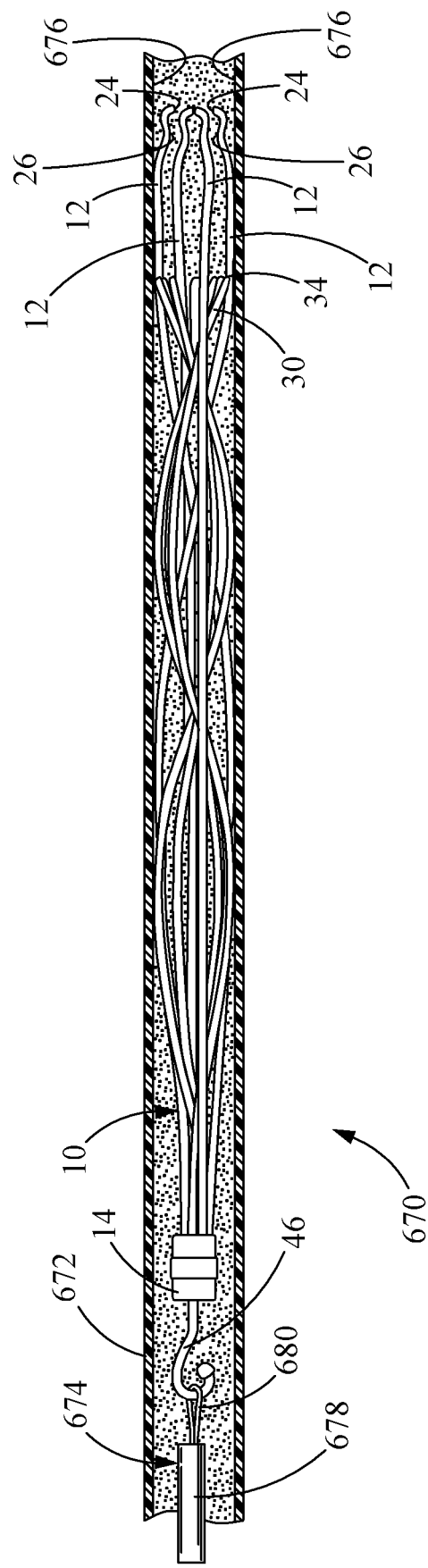
FIG. 4 is a side cross-sectional view of a removable filter assembly, according to the principles of the present invention.

Now with reference to FIG. 4, a portion of a removable filter assembly 670 is illustrated. The removable filter assembly 670 includes a filter 10 and a tube 672. The filter 10 is illustrated in a collapsed state and disposed in the tube 672 for delivery or retrieval. The tube may be a catheter formed of a flexible material. Although shown with the filter 10 of FIG. 1, it should be understood that any filter 10 contemplated within the scope of the claims of the present invention could be used.

As shown, the filter 10 is shaped for each primary strut 12 to cross another primary strut 12 along the longitudinal axis X. As a result, in the collapsed state, the anchoring hooks 24 are configured to be inverted or inwardly faced or positioned along the longitudinal axis X and away from the walls of a blood vessel for retrieval and delivery of the filter 10. This inverted or inwardly facing configuration of the anchoring hooks 24 allows for simplified delivery and retrieval of filter 10. For example, a concern that the anchoring hooks 24 in the collapsed state may scrape, scratch, or tear the inner wall of a delivery/retrieval tube is eliminated, since the filter 10 of the present invention is shaped to have the anchoring hooks 24 inwardly face or positioned along the longitudinal axis away from the blood vessel. In fact, a set of inner and outer delivery/retrieval sheaths may be eliminated during the delivery or retrieval of the filter 10 through the jugular vein. Rather, merely one tube 672 with a loop snare mechanism 674 may be used to deliver or retrieve the filter 10 of the present invention.

Moreover, in the collapsed state, each primary strut 12 is configured to cross another primary strut 12 along the longitudinal axis X such that the anchoring hooks 24 and the resistant portions 26 are located away from the wall 676 of the tube 672 in the collapsed state.

In this embodiment of the present invention, it is to be noted that the filter 10 may be delivered or retrieved by any suitable introducer (delivery or retrieval) tube 672. However, it is preferred that the tube 672 has an inside diameter of between about 4.5 French and 16 French, and more preferably between about 6.5 French and 14 French.

For deployment of the filter 10, the tube 672 is percutaneously inserted through the patient's vessel such that the distal end of the tube 672 is at the location of deployment. In some embodiments, a wire guide is preferably used to guide the tube 672 to the location of deployment. The filter 10 is inserted through the proximal end of the tube 672 with the removal hook 46 leading and anchoring hooks 24 of the primary struts 12 held by a filter retainer member for delivery via the femoral vein of a patient. For delivery via the jugular vein of a patient, the filter 10 is inserted through the proximal end of the tube 672 with the anchoring hooks 24 of the primary struts 12 leading and the removal hook 46 trailing. In this embodiment, a pusher wire having a pusher member at its distal end may be fed through the proximal end of the tube 672 thereby pushing the filter 10 until the filter 10 reaches the distal end of the tube 672 to a desired location.

During deployment, the secondary struts 30 expand first to centralize or balance the filter 10 within the vessel. When the free ends 34 of the secondary struts 30 emerge from the distal end of the tube 672, the secondary struts 30 expand to an expanded position as shown in FIG. 1. The second arcs 42 engage the inner wall of the vessel. The second arcs 42 of the secondary struts 30 function to stabilize the attitude of filter 10 about the center of the blood vessel. When delivering through the jugular vein, the filter 10 is then pushed further by the pusher wire (not shown) until it is fully deployed.

When the filter 10 is fully expanded in the vena cava, the anchoring hooks 24 of the primary struts 12 and the second arcs 42 of the secondary struts 30 are in engagement with the vessel wall. Further, the resistant portions 26 proximate the anchoring hooks 24 are in contact with the vessel wall, exerting pressure thereon, and thereby decreasing the amount of pressure exerted by the anchoring hooks 24 and the amount of penetration of the anchoring hooks 24. The anchoring hooks 24 of the primary struts 12 have anchored the filter 10 at the location of deployment in the vessel, preventing the filter 10 from moving with the blood flow through the vessel. As a result, the filter 10 is supported by two sets of struts 12, 30 that are spaced axially along the length of the filter 10.

When deployed, the hub 14 and retrieval hook 46 are positioned downstream from the location at which the anchoring hooks 24 are anchored in the vessel. When captured by the struts 12, 30, thrombi remains lodged in the filter 10. The filter 10 along with the thrombi may then be percutaneously removed from the vena cava. When the filter 10 is to be removed, the removal hook 46 is preferably grasped by a retrieval instrument that is percutaneously introduced in the vena cava in the direction of retrieval hook 46 first. The anchoring hooks 24, with the help of the resistant portions 26, are configured to be retracted from the blood vessel, avoiding tissue removal from the blood vessel. In other words, the removal of the struts 12 is atraumatic, avoiding tearing of tissue from the vessel wall.

The primary and secondary struts can be formed from any suitable material that will result in a self-opening or self-expanding filter, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives.

In other embodiments, both the primary struts and the secondary struts are made from Nitinol with a transition temperature that is slightly below normal body temperature of humans, which is about 98.6° F. Thus, when the filter is deployed in the vena cava and exposed to normal body temperature, the alloy of the struts will transform to austenite, that is, the remembered state, which for the present invention is an expanded configuration when the filter is deployed in the blood vessel. To remove the filter, the filter is cooled to transform the material to martensite which is more ductile than austenite, making the struts more malleable. As such, the filter can be more easily collapsed and pulled into the sheath for removal.

In certain embodiments, both the primary struts and the secondary struts are made from Nitinol with a transition temperature that is above normal body temperature of humans, which is about 98.6° F. Thus, when the filter is deployed in the vena cava and exposed to normal body temperature, the struts are in the martensitic state so that the struts are sufficiently ductile to bend or form into a desired shape, which for the present invention is an expanded configuration. To remove the filter, the filter is heated to transform the alloy to austenite so that the filter becomes rigid and returns to a remembered state, which for the filter is a collapsed configuration in this embodiment.

The primary and secondary struts form a netting pattern that functions to catch thrombi carried in the blood stream prior to reaching the heart and lungs to prevent the possibility of a pulmonary embolism. The netting pattern is sized to catch and stop thrombi that are of a size that are undesirable to be carried in the vasculature of the patient. Due to its compacted size, the hub minimally resists blood flow. The netting pattern may include the primary struts and secondary struts at substantially equal angular space relative to each other. In such a configuration, the netting pattern provides an even distribution between the primary and secondary struts to the blood flow, increasing the likelihood of capturing thrombi. However, it should be understood that other netting patterns are also available, without falling beyond the spirit and scope of the present invention. For example, the netting pattern may include uneven or unequal spacing between the primary and secondary struts.

With reference to FIG. 1, the free ends of the primary struts 12 (which include the anchoring hooks 24) and the distal ends 34 of the secondary struts 30 extend in a common axial direction from the hub 14. In other words, they extend from the same side of the hub 14. The secondary struts 30, however, are shorter in length than the primary struts 12. The resistant portion 26 is disposed along the length of the primary strut 12 at a point axially displaced from the secondary struts 30 with reference to the longitudinal axis X. Thus, the resistant portions 26 are disposed directly next to the anchoring hooks 24 on the primary struts 12 at a point axially removed from the secondary struts 30, in this embodiment.

To remove the filter 10 from the inferior vena cava or other blood vessel, a retrieval device including a retrieval tube, which may be similar to the tube 672, may be used. The retrieval tube 672 may be percutaneously introduced into the superior vena cava via the jugular vein. In this procedure, the retrieval tube 672 is inserted into the superior vena cava. A wire 678 having a loop snare 680 at its distal end is threaded through the retrieval tube 672 and is exited through the distal end of the tube 672. The wire 678 is then manipulated by any suitable means from the proximal end of the retrieval tube 672 such that the loop snare 680 captures the removal hook 46 of the filter 10. Using counter traction by pulling the wire 678 while pushing the retrieval tube 672, the retrieval tube 672 is passed over the filter 10. As the retrieval tube 672 passes over the filter 10, the primary struts 12 and then the secondary struts 30 engage the edge of the retrieval tube 672 and are caused to pivot or undergo bend deflection at the hub 14 toward the longitudinal axis X of the filter 10. The pivoting toward the longitudinal axis X causes the ends of the struts 12, 30 to be retracted from the vessel wall, including retracting the anchoring hooks 24 from the vessel wall. In this way, the vessel wall remains substantially undamaged in the removal procedure. However, it is to be noted that any other suitable procedure may be implemented to remove the filter from the patient.

Although the embodiments of this device have been disclosed as being constructed from wire having a round cross section, it could also be cut from a tube of suitable material by laser cutting, electrical discharge machining or any other suitable process.

While the present invention has been described in terms of preferred embodiments, it will be understood, of course, that the invention is not limited thereto since modifications may be made to those skilled in the art, particularly in light of the foregoing teachings.

What we claim is:

1. A removable filter for capturing thrombi in a blood vessel, the filter comprising:

a plurality of primary struts having first ends attached together along a longitudinal axis of the filter, each primary strut having a body member extending from the first end along the longitudinal axis to an anchoring hook at a terminal end of the primary strut, the body member having a proximal portion and a distal portion, each primary strut being configured to move relative to the longitudinal axis between an expanded state for engaging with the blood vessel and a collapsed state for filter delivery or retrieval, at least one primary strut having first and second bends proximate the anchoring hook, the first bend being disposed distally to the second bend, the distal portion of the body member extending from the first bend to the anchoring hook, the first bend having a first concave side and a first convex side, the second bend having a second concave side and a second convex side, the body member having an outer side that faces away from the longitudinal axis in the expanded state, the first convex side of the first bend extending from the outer side of the body member and away from the longitudinal axis, the second concave side of the second bend being disposed on the outer side of the body member, a substantial portion of the outer side of the distal portion of the body member being substantially tangent to the first convex side of the first bend, the first convex side of the first bend being configured to contact the blood vessel in the expanded state; and a plurality of secondary struts having proximal ends attached together along the longitudinal axis and distal ends located radially from the longitudinal axis in the expanded state, the plurality of secondary struts being configured to engage the blood vessel to centralize the filter in the expanded state in the blood vessel.

2. The removable filter of claim 1, wherein the body member is an arcuate segment including a first curved portion and a second curved portion, the first curved portion extending from the first end, the second curved portion extending from the first curved portion and extending to the second bend, the second curved portion having a body member arc radius, the first bend having a first bend arc radius, the first bend arc radius being smaller than the body member arc radius.

3. The removable filter of claim 2, wherein the first curved portion is configured to extend radially from the longitudinal axis of the filter in a concave curve toward an inflection point, and the second curved portion is configured to extend radially from the inflection in a convex curve in the expanded state.

4. The removable filter of claim 1, wherein the first bend is configured to apply pressure to the blood vessel to decrease the pressure applied to the blood vessel by the anchoring hook.

5. The removable filter of claim 4, the body member being configured to extend from each side of the first bend away from the blood vessel in the expanded state.

6. The removable filter of claim 4, wherein the first bend has an arcuate shape.

7. The removable filter of claim 4, wherein the body member is configured to extend from each side of the first bend, a first side of the body member configured to extend from the first bend away from the vessel wall in the expanded state, and a second side of the body member configured to extend from the first bend to the anchoring hook and remain in contact with the vessel wall in the expanded state.

8. The removable filter of claim 7, wherein a proximal portion of the body extends at an angle in the range of about 135 degrees to about 155 degrees with respect to a distal portion of the body member, the proximal and distal portions being separated by the first bend.

9. The removable filter of claim 1, each anchoring hook having a constant angle with respect to the longitudinal axis.

10. The removable filter of claim 1, each primary strut contacting other primary struts only at a central hub in the expanded state.

11. The removable filter of claim 1, each primary strut having a single anchoring hook.

12. The removable filter of claim 1, each secondary strut having a first arc extending from the proximal end and a second arc extending from the first arc to the distal end, the distal end being a free end, the second arc being configured to engage the blood vessel to centralize the filter in the expanded state in the blood vessel, a hub having a sleeve configured to axially house the first ends of the plurality of primary struts, the removable filter further comprising a retrieval hook extending from the hub opposite the plurality of primary struts for removal of the filter from the blood vessel.

13. The removable filter of claim 1, free ends of the primary struts and the distal ends of the secondary struts extending in a common axial direction from the hub, the secondary struts being shorter in length than the primary struts, wherein the first and second bends are disposed along the length of the primary strut at a point axially displaced from the secondary struts with reference to the longitudinal axis.

14. The removable filter of claim 1, wherein each primary strut terminates at its anchoring hook.

15. The removable filter of claim 1, wherein the first and second bends separate two approximately parallel portions of the body member.

16. The removable filter of claim 1, the first bend having a semicircular shape.

* * * * *